United States Patent [19]

Klokkers-Bethke et al.

[11] Patent Number: 5,744,124

[45] Date of Patent: Apr. 28, 1998

[54] NITROGLYCERIN-CONTAINING HYDROPHILIC AQUEOUS PUMPABLE SPRAY COMPOSITION

[75] Inventors: Karin Klokkers-Bethke, Rödermark; Ulrich Münch, Monheim/Rhld., both of Germany

[73] Assignee: Schwarz Pharma AG, Monheim, Germany

[21] Appl. No.: 890,314

[22] Filed: May 26, 1992

Related U.S. Application Data

[63] Continuation of Ser. No. 731,126, Jul. 15, 1991, abandoned.

[30] Foreign Application Priority Data

Aug. 17, 1990 [DE] Germany ................. 4026072.0

[51] Int. Cl.[6] ..................... A61K 9/12; A61K 31/04
[52] U.S. Cl. ..................... 424/47; 424/43; 514/509
[58] Field of Search ................. 424/401, 43, 44, 424/47; 514/509; 558/486

[56] References Cited

U.S. PATENT DOCUMENTS

| | | | |
|---|---|---|---|
| 3,155,574 | 11/1964 | Silson et al. | 167/54 |
| 4,323,577 | 4/1982 | Ohkuma et al. | 514/509 |

FOREIGN PATENT DOCUMENTS 0 310 910 A1  4/1989  European Pat. Off. .

*Primary Examiner*—Robert H. Harrison
*Attorney, Agent, or Firm*—Marshall, O'Toole, Gerstein, Murray & Borun

[57] ABSTRACT

A hydrophilic aqueous pump spray composition for treating angina pectoris comprising 0.15 to 0.50 weight/% of nitroglycerin, 24.50 to 24.85 weight/% of ethanol, 32.00 weight/% of 1,2-propyleneglycol and 43.00 weight/% of purified water and having a pH of 3 to 6; a method of producing the composition; and, a product comprising a container having the composition as a solution therein and provided with a dosage dispensing pump.

9 Claims, No Drawings

NITROGLYCERIN-CONTAINING HYDROPHILIC AQUEOUS PUMPABLE SPRAY COMPOSITION

This application is a continuation of application Ser. No. 07/731,126, filed Jul. 15, 1991, now abandoned.

This invention pertains to a nitroglycerin-containing, propellant-free, hydrophilic aqueous pump spray composition for treating angina pectoris, a method of producing the composition and a product comprising a container having the composition therein, with the container desirably provided with a dosage dispensing pump.

BACKGROUND OF THE INVENTION

Nitroglycerin, also called glyceroltrinitrate (GTN), is an active substance for the treatment of angina pectoris attacks. Among other things, it is used in emergency situations in which the medication must be fact acting.

The pharmaceutical agents used for this specific purpose, such as sublingual tablets or crunchable capsules, have disadvantages. A disadvantage, amongst others, is that after intake the active agent in these pharmaceutical agents must first be released and dispersed prior to being available for resorption in dissolved form. Furthermore, the loss of time needed to take the pharmaceutical agent out of a blister package can be critical during an acute angina attack.

To avoid the disadvantages of the described pharmaceutical forms, nitroglycerin-containing sprays have been developed. By spraying a dose of the active agent into the buccal area of the mouth, a direct and rapid dispersion of a solution of the active agent over as large a portion as possible of the oral mucosa, which absorbs the active agent nitroglycerin, was to be achieved. In this way, a large area was to be reached, thereby accelerating absorption of the active agent.

Sprays containing a propellant, however, have many disadvantages. The low molecular weight haloalkanes used as propellants have a detrimental effect on the environment. Thus, there is a connection between the use of fluorochlorohydrocarbon propellants and the reduction of the ozone layer in the upper atmosphere. Therefore, many countries limit the use of haloalkanes as propellants.

With respect to the field of application, if nitroglycerin-containing propellant sprays are administered during the treatment of acute angina pectoris, these propellants cause an undesirable drying-out effect in the mouth. Since the mouth usually exsiccates during an angina pectoris attack, the drying-out effect caused by the propellant is particularly disadvantageous.

Based on the substance-specific characteristics of nitroglycerin, many nitroglycerin-containing preparations have been described which contain a carrier substance system based on fats and oils. However, these preparations must contain at least one preserving agent to protect them against decomposition, oxidation, or the fatty acid-containing triglycerides from becoming rancid. These types of additives in medications are not only undesirable per se, but also because of their ability to initiate allergic responses.

Furthermore, lipophilic solvents prevent the nitroglycerin from being distributed with the desired promptness in the hydrophilic mucosa of the mouth during acute attacks of angina pectoris.

In the past the amount of lipophilic solvents used has been reduced to increase the availability of the active substance in propellant-containing dosing aerosols. However, the surge duration, measurable via the maximum plasma concentration ($c_{max}$) and the time of the maximum concentration ($t_{max}$), was only insignificantly effected.

It is reported that P. M. Dewland et al. [Heart and Vessels, 7, 536–544 (1987)] obtained higher $c_{max}$ values (Table 1 a.a.O) for three nitroglycerin sprays, manufactured with lipophilic solutions, by decreasing the amount of the lipophilic formulation portions; however, the $t_{max}$ was not significantly different.

Another approach is to increase the concentration of nitroglycerin in the product as is described in the DE-A 32 46 081. By means of the formulation disclosed in this reference, the propellant portion is increased to 60–95% by weight of the formulation. The increased propellant portion permits higher concentrations of nitroglycerin in the non-volatile oily solvents.

A disadvantage of such formulations, however, is that the medicament must first diffuse into the mucosa from the oily substance solution. Because of this the surge of the active agent, which is important when an angina attack occurs, cannot be significantly shortened. Also, for reasons of increased environmental awareness, it is undesirable to increase the amount of propellant which, therefore, should be avoided.

A qualitatively significant improvement in the action of sprays administered during an angina attack is not possible when the lipophilic solvents are used in propellant-containing dosing aerosols.

Another possibility for quickly distributing the nitroglycerin in the hydrophilic mucosa is by use of a solution which mixes with the mouth aqueous mucosa. In this regard, one must take into consideration that the spray formulation solution be desensitized sufficiently and also be technically easy to handle with respect to production requirements.

U.S. Pat. No. 3,155,574 describes a nitroglycerin inhalation spray formulation containing a propellant and a hydrophilic solvent base which contains nitroglycerin, 1,2-propanediol and water-free, or absolute, ethanol. However, inhalation is unnecessary since nitroglycerin is sufficiently absorbed through the oral mucosa. Actually, with inhalation there is a reduction in the expected increase in nitroglycerin bio-availability by the first pass of the drug through the lungs. In addition, it is extremely difficult for the patient to inhale during the angina attack.

Investigations by H. Laufen et al. in [Therapy Week, 34, 963–970 (1984)] showed that in the case of hydrophilic formulations as compared to lipophilic-based nitroglycerin sprays, the occurrence of the active agent in the blood, as well as the amount of the resorbed substance, is faster and larger. The composition of the preparation and the dosing system, however, were not disclosed.

EP 0310 910 describes a hydrophilic nitroglycerin spray formulation which is free of fluorochlorohydrocarbons and which, besides the nitroglycerin, contains only ethanol and water as the carrier solvent. However, the lack of desensitization of the nitroglycerin in this formulation is detrimental. If the solvent evaporates, during which the ethanol content in particular is reduced, the nitroglycerin settles as an oily phase in the form of drops at the bottom of the bottle. Furthermore, the formulation requires the use of nitroglycerin dissolved in ethanol, with the combustibility disadvantage and the instability danger possessed by this raw material.

DE-OS 39 22 650 describes as the object of its invention, a nitroglycerin-containing, propellant-free aerosol preparation consisting of nitroglycerin and 51 to 90% of one or more aliphatic alcohols having 2 to 4 carbon atoms and 10 to 49% of polyalkyleneglycols or 1 to 3 valent alcohols having 2 to 8 carbon atoms and 1, 2 or 3 hydroxyl groups. The dosage system or method of administration used were not stated.

The high content of one or more aliphatic alcohols having 2 to 4 carbon atoms in this formulation is disadvantageous. The degree of evaporation of the alcohol, and the volatility of the formulation component parts from commercial dosage pumps, is high so that when the spray is not used for a long period of time, the composition changes so that the composition administered during an attack does not correspond to the pharmaceutical formulation originally present in the storage container. Finally, the high percentage of alcohol is detrimental from an economic point of view as well, since alcohol is an expensive raw material.

It is also stated that one can use up to 49% of polyalkyleneglycols in the formulation. However, whenever possible one should avoid polymer substances as carriers in pharmaceutical preparations since they contain contaminants such as initiator molecules, di- and tripolymers and catalyst residues. These contaminants are not safe because of their physiological effects.

Furthermore, the above mentioned spray formulations containing nitroglycerin according to the prior art, have a disadvantage in that they deliver variable volumes of the formulation which contain nitroglycerin concentrations which are not uniform per spray puff or shot.

SUMMARY OF THE INVENTION

According to the invention a nitroglycerin-containing hydrophilic aqueous pumpable spray composition is provided which contains no propellants and which supplies a therapeutically effective level of nitroglycerin to the blood in the shortest possible time, even after the composition is in storage a long time or after repeated usage. The invention also provides a method of making the composition and products containing the composition for administration to a patient.

Surprisingly, it has been found that a sprayable preparation having a composition according to this invention comprising 0.15 to 0.50 weight/% of nitroglycerin, 24.50 to 24.85 weight/% of ethanol, 32.00 weight/% of propylene glycol, and 43.00 weight/% of purified water, adjusted to pH 3–6, has a favorable pharmacokinetic behavior for the treatment of an angina pectoris attack with a fast surge and high bio-availability and that the preparation is chemically extremely stable. Even after a long storage time, or repeated use at short intervals, the preparation is pharmaceutically guaranteed. Because of the specified content of alcohols, and despite the presence of water, the preparation does not have to be preserved. This is another advantage of the preparation since preservatives often induce allergic responses.

The spray preparation advantageously can contain 0.30 weight/% of nitroglycerin, 24.70 weight/% of ethanol, 32.00 weight/% of 1,2-propyleneglycol and 43.00 weight/% of purified water, adjusted to pH 6.

Preferably, the spray preparation can contain 0.40 weight/% of nitroglycerin, 24.60 weight/% of ethanol, 32.00 weight/% of 1,2-propyleneglycol and 43.00 weight/% of purified water, adjusted to pH 6.

Preparations according to this invention can be used in pump atomizer dosage apparatus due to their relatively low vapor pressure which is determined by the components used in the composition. In this way that advantage which is possessed by the nitroglycerin spray containing the propellant PCKW as is disclosed in DE-P3246081, as well as the ability to supply a uniform dosage independent of the storage time subsequent to a previous use, are retained.

A specific embodiment of a spray according to this invention, adjusted to pH 6, has the following composition:

| | |
|---|---|
| Nitroglycerin | 0.30% |
| Ethanol | 24.70% |
| 1,2-propyleneglycol | 32.00% |
| Purified Water | 43.00% |

The preparations fulfill the quality requirements of medicaments based on the qualitative and quantitative compositions of the mixtures. Even during the usual cold winter temperatures, the nitroglycerin does not separate.

The spray formulations or preparations provided by this invention can be produced using customary drug industry manufacturing methods and technologies. Thus, a spray formulation according to this invention can be produced by mixing together 0.15–0.50 weight/% of nitroglycerin, 24.50–24.85 weight/% of ethanol, 32.00 weight/% of 1,2-propyleneglycol and 43.00 weight/% of purified water. The resulting solution is then filled into primary packaging means comprising a container having a dosage pump equipped with a spray head to make a finished product.

According to a specific embodiment of the method according to this invention, 0.30 weight/% of nitroglycerin, 24.70 weight/% of ethanol, 32.00 weight/% of 1,2-propyleneglycol and 43.00 weight/% of purified water are mixed together, the resulting solution is adjusted to pH 6 and then packed in suitable primary packaging means such as described above.

According to another advantageous embodiment of the method according to this invention, 0.40 weight/% of nitroglycerin, 24.60 weight/% of ethanol, 32.00 weight/% of 1,2-propyleneglycol and 43.00 weight/% of purified water are mixed, the resulting solution is adjusted to pH 6 and then packed into a suitable primary packaging means.

The following examples are presented to further illustrate the invention.

EXAMPLE 1 a) 0.60 g of a propyleneglycol-containing nitroglycerin solution, formed from 30 mg of nitroglycerin and 570 mg of 1,2-propyleneglycol, was mixed with 2.50 g of ethanol, 2.63 g of 1,2-propyleneglycol and 4.30 g of purified water and then stirred until it had a homogeneous consistency. Thereafter, 0.1N hydrochloric acid was added drop-by-drop until the solution was at pH 6.

The resulting solution was filtered through a PVDF-Filter (pore size 0.22 μm) from Millipore. Then the solution was filled into a Braun glass bottle. A dosage pump with spray head was then screwed onto the bottle.

b) Alternatively, the solution can be filled into an aerosol glass bottle, onto which a dosage pump with spray head is crimped on.

EXAMPLE 2 a) 0.60 g of an alcoholic nitroglycerin solution, formed from 30 mg of nitroglycerin and 570 mg of ethanol, is mixed with 1.90 g of ethanol, 3.20 g of 1,2-propyleneglycol and 4.30 g of purified water and stirred until it had a homogeneous consistency. Thereafter 0.1N hydrochloric acid was added drop-by-drop until the solution was at pH 6. The resulting solution was filtered through a PVDF-9 Filter (pore size 0.22 µm) from Millipore. Then the solution was filled into a Braun glass bottle onto which was screwed a dosage pump with spray head.

b) Alternatively, the described solution can be filled into an aerosol glass bottle, onto which is crimped a dosage pump with spray head.

EXAMPLE 3 a) 0.80 g of an alcoholic nitroglycerin solution, formed from 40 mg of nitroglycerin and 760 mg of water-free ethanol, was mixed with 1.70 g of ethanol, 3.20 g of 1,2-propyleneglycol and 4.30 g of purified water and stirred until it reached a homogeneous consistency. Then 0.1N hydrochloric acid was added drop-by-drop until the solution was adjusted to pH 6. The resulting solution was filtered through a PVDF-Filter (pore size 0.22 µm) from Millipore. Thereafter, the solution was filled into a Braun glass bottle onto which was screwed a dosage pump with spray head.

b) Alternatively, the solution can be filled into an aerosol glass bottle onto which is crimped a dosage pump with spray head.

A pump spray preparation according to this invention provides the following advantages and benefits:

1. It is environmentally friendly since it does not use a propellant.
2. Since it need not contain a preservative no allergic reactions are induced when it is used.
3. It contains no polymer components so that no initiator molecules or catalyst residues having harmfull physiological effects are present.
4. It has a long shelf life.
5. After a long storage period or period of non-use, or several consecutive dosage applications, a constant dosage output amount of uniform composition is provided.

These beneficial characteristics of a pump spray preparation according to this invention have been established by pharmacokinetic investigations.

In a bio-availability study, a panel of 15 persons in a random cross test were each given 0.10 ml of a spray (A) according to this invention, a water-free spray preparation (B) as well as a commercial sublingual tablet of the same dosage, and the blood level was determined 1,2,3,4,5,6,7, 10,20 & 30 minutes after administration. The commercially available sublingual tablet Nitropen® consisted of 0.3 mg of nitroglycerin and the customary tablet adjuvants. The spray (A) had the composition described in Example 2. The water-free spray (B) had a composition of 0.377 weight/% of nitroglycerin, 89.623 weight/% of ethanol and 10.0 weight/% of 1,2-propyleneglycol.

The result of the bio-availability study is summarized in Table 1.

TABLE 1

|  | AUC (1) [mg/ml] | $C_{max}$ [mg/ml] | $t_{max}$ [Min] |
|---|---|---|---|
| Sublingual tablet | 23.408 | 3.053 | 5.667 |
| Spray (A) | 24.797 | 2.938 | 3.667 |
| Water-free spray (B) | 22.601 | 3.633 | 4.333 |

(1) Area under graph curve.

The spray (A) according to this invention yielded the shortest surge (shortest $t_{max}$) in the pharmacokinetic study while the sublingual tablet showed the slowest surge and the longest $t_{max}$. The water-free spray (B) lies between those two formulations.

The result of this study proves that, in a surprising manner, the surge speed can be decisively influenced by the active agent via the solution characteristics of the formulation so that the patient receives fast relief during an angina attack and prompt analgesia.

Surprisingly, formulation (A) according to this invention proved superior to the formulation (B) in function tests using commercial pump dosage atomizers:

TABLE 2

| Storage position of the pump dosage atomizer | Evaporation losses after 50 days storage at room temperature | |
|---|---|---|
|  | Spray (A) [mg] | Spray (B) [mg] |
| Upright | 3.6 ± 3.7 | 30.6 ± 26.1 |
| Horizontal position | 12.2 ± 6.8 | 118.5 ± 37.6 |
| Upside down | 12.1 ± 7.5 | 58.9 ± 30.1 |

Spray (A) according to this invention had an insignificant weight loss of about 270 mg, at the very most, during a customary life of three years for medications under the most unfavorable storage position. On the other hand, the comparative spray (B) may suffer 2.6 g of weight loss in three years, which shortens the useful life of the medicament.

With an amount of about 10 to 20 g of solution per spray container, an acceptable stability with respect to the quality and quantity of the medication is only achieved with solution (A) according to this invention.

Pump dosage apparatus used to atomize solutions to be administered for vital purposes, such as the treatment of an angina pectoris attack, must meet stringent requirements. For example, the availability of the next dosage must be guaranteed following an interval after the previous spray dosage. Most commercial dosage pumps must be pumped several times following a period of nonuse, such as a standing time of only part of one day, since the dosage chamber is not sealed so that the content thereof can freely evaporate. In a dosage pump which seals off the content of the dosage chamber the pump priming can be omitted due to this construction.

Spray or solution (A) previously described herein when used in a pump spray apparatus will provide a full dosage from the first spray onward, regardless of the length of time during which the preparation is out of use from when a previous dosage was administered by use of the pump spray. Previous commercial spray formulations lack this ability, even when used in pump sprays having a dosage chamber closure, because evaporation losses can occur due to the surface tension of the solution to be dosed, the solution vapor pressure and the swelling or shrinkage effect caused by the solution on the pump parts.

A comparative investigation of spray (A) provided by this invention and customary spray formulations showed that spray (A) after 36 days of non-use provided the necessary dosage amount during the first spray dosage. It amounted to 81.8%±6.8% of the medium output amount of twelve (12) pump sprays.

What is claimed is:

1. A medicinal product for the buccal administration of nitroglycerin to a patient in need of nitroglycerin therapy comprising:
    a container having a pump spray means for dispensing a spray dosage of a composition in the container into the buccal area of a patient's mouth;
    the composition being a hydrophilic aqueous pump spray composition comprising 0.15 to 0.50 weight/% of nitroglycerin, 24.50 to 24.85 weight/% of ethanol, 32.00 weight/% of 1,2-propyleneglycol and 43.00 weight/% of purified water and having a pH of 3 to 6; and the composition and the container containing no propellant.

2. A medicinal product according to claim 1 in which the hydrophilic aqueous pump spray composition comprises 0.30 weight/% of nitroglycerin, 24.70 weight/% of ethanol, 32.00 weight/% of 1,2-propyleneglycol and 43.00 weight/% of purified water with a pH value of 6.

3. A medicinal product according to claim 1 in which the hydrophilic aqueous pump spray composition comprises 0.40 weight/% of nitroglycerin, 24.60 weight/% of ethanol, 32.00 weight/% of 1,2-propyleneglycol and 43.00 weight/% of purified water with a pH value of 6.

4. A method of manufacturing a medicinal product for the buccal administration of nitroglycerin to a patient in need of nitroglycerin therapy comprising:

mixing together 0.15 to 0.50 weight/% of nitroglycerin, 24.50 to 24.85 weight/% of ethanol, 32.00 weight/% of 1,2-propyleneglycol and 43.00 weight/% of purified water to form a hydrophilic aqueous pump spray composition;

adjusting the composition to a pH value of 3 to 6;

filling the composition into a container and closing the container with a pump spray means for dispensing a spray dosage of the composition into the buccal area of a patient's mouth; and the composition and the container containing no propellant.

5. A method according to claim 4 in which:

the composition comprises 0.30 weight/% of nitroglycerin, 24.70 weight/% of ethanol, 32.00 weight/% of 1,2-propyleneglycol and 43.00 weight/% of purified water.

6. A method according to claim 4 in which:

the composition comprises 0.40 weight/% of nitroglycerin, 24.60 weight/% of ethanol, 32.00 weight/% of 1,2-propyleneglycol and 43.00 weight/% of purified water.

7. A method of treating a patient in need of nitroglycerin therapy comprising:

spraying a dosage amount of a hydrophilic aqueous pump spray composition from a container having the composition therein, said spray being produced solely by means of a pump means operatively associated with the container and with the composition and container containing no propellant, into the buccal area of a patient's mouth;

said composition comprising 0.15 to 0.50 weight/% of nitroglycerin, 24.50 to 24.85 weight/% of ethanol, 32.00 weight/% of 1,2-propyleneglycol and 43.00 weight/% of purified water and having a pH of 3 to 6.

8. A method according to claim 7 in which:

the composition comprises 0.30 weight/% of nitroglycerin, 24.70 weight/% of ethanol, 32.00 weight/% of 1,2-propyleneglycol and 43.00 weight/% of purified water with a pH value of 6.

9. A method according to claim 7 in which:

the composition comprises 0.40 weight/% of nitroglycerin, 24.60 weight/% of ethanol, 32.00 weight/% of 1,2-propyleneglycol and 43.00 weight/% of purified water with a pH value of 6.

* * * * *